United States Patent
Gharib et al.

(10) Patent No.: US 10,946,148 B2
(45) Date of Patent: Mar. 16, 2021

(54) METHOD AND APPARATUS FOR THE PRODUCTION OF MICROSCALE BUBBLES BY DEPRESSURIZATION CAVITATION

(71) Applicant: California Institute of Technology, Pasadena, CA (US)

(72) Inventors: Morteza Gharib, Pasadena, CA (US); Daegyoum Kim, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 16/134,136

(22) Filed: Sep. 18, 2018

(65) Prior Publication Data

US 2019/0015604 A1 Jan. 17, 2019

Related U.S. Application Data

(63) Continuation of application No. 13/089,910, filed on Apr. 19, 2011, now abandoned.

(60) Provisional application No. 61/325,881, filed on Apr. 20, 2010.

(51) Int. Cl.
*A61M 11/00* (2006.01)
*B05B 7/00* (2006.01)

(52) U.S. Cl.
CPC ........... *A61M 11/00* (2013.01); *A61M 11/007* (2014.02); *B05B 7/0018* (2013.01); *A61M 2202/0468* (2013.01)

(58) Field of Classification Search
CPC ................ A61M 11/00; A61M 11/007; A61M 2202/0468; B05B 7/0018
USPC ......................................................... 424/400
See application file for complete search history.

(56) References Cited

U.S. PATENT DOCUMENTS

| | | | |
|---|---|---|---|
| 4,981,178 A | 1/1991 | Bundy | |
| 5,314,644 A | 5/1994 | Michelsen | |
| 5,484,525 A | 1/1996 | Mowka, Jr. | |
| 6,042,089 A * | 3/2000 | Klein | B01F 5/0403 261/76 |
| 6,966,942 B2 | 11/2005 | Broadbent | |
| 2006/0060991 A1* | 3/2006 | Holsteyns | B08B 3/12 261/81 |
| 2007/0119987 A1 | 5/2007 | Vion | |
| 2007/0267334 A1* | 11/2007 | Osborn | B01F 3/0473 210/97 |
| 2008/0189847 A1 | 8/2008 | Yamasaki et al. | |
| 2008/0194868 A1 | 8/2008 | Kozyuk | |
| 2010/0069281 A1 | 3/2010 | Guignot et al. | |
| 2011/0284648 A1 | 11/2011 | Gharib et al. | |

FOREIGN PATENT DOCUMENTS

| | | |
|---|---|---|
| WO | 2011133533 A2 | 10/2011 |
| WO | 2011133533 A3 | 10/2011 |

OTHER PUBLICATIONS

Hirai et al., non-patent literature, title: development of high density micro-bubble generator for environmental technology; Electronics and Electrical Engineering, vol. 92. Issue 4, p. 37-40, 2009. (Year: 2009).*
Koichi Sasaki, et al; title: Effect of Pressurization on the Dynamics of a Cavitation Bubble Induced by Liquid-Phase Laser Ablation; The Japan Society of Applied Physics, Applied Physics Express 2, pp. 04650-1 to 04650-3, published online Mar. 27, 2009. (Year : 2009).*
Unknown author, title: Dawn Ultra Dishwashing Liquid, Original Scent; downloaded from https://dawn-dish.com/en-us/products/by-line/dawn-ultra on Aug. 20, 2020. (Year: 2020).*
Nyco, title: Simple Science: The Difference Between Soap and Detergent; downloaded from https://www.nycoproducts.com/resources/blog/simple-science-the-difference-between-soap-and-detergent on Aug. 20, 2020. (Year: 2020).*
Donny Quinn, title: Ingredients in Dawn Dish Detergent, Jul. 21, 2017. (Year: 2017).*
Parhizkar, et al, title: The effect of surfactant type and concentration on the size and stability of microbubbles produced in a capillary embedded T-junction device; RSC Adv., 2015, vol. 5, pp. 10751-10762. First published Dec. 19, 2014. (Year: 2014).*
International Preliminary Report on Patentability for International Application No. PCT/US2011/033026, dated Oct. 23, 2012, 6 pgs.
International Search Report and Written Opinion for International Application PCT/US2011/033026, completed Dec. 27, 2011, 8 pgs.
Household Products Database, Health and Safety Information on Household Products. Retrieved from http://householdproducts.nlm.nih.gov/cgi-bin/household/brand?tbl=chem&id=78 17 pgs.
Forgco_Admin (Unknown), "Misting nozzles explained", published Oct. 23, 2012, 3 pgs.
Kauffer et al., "sodium lauryl sulfate", published Mar. 2010. 3 pgs.
Rosen et al., "Surfactants", Particle Sciences, Technical Brief, 2010, vol. 1, 2 pgs.
Sou et al., "Effects of cavitation in a nozzle on liquid jet atomization", Int. J. Heat and Mass Transfer, 2007, vol. 50, pp. 3575-3582.
Wikipedia, "Surface tension", Retrieved from https://en.wikipedia.org/wiki/Surface_tension, 21 pgs.
Zhou et al., "Role of Hydrodynamic cavitation in fine particle floatation", Int. J. Miner Process, 1997, vol. 51, pp. 140-142.

* cited by examiner

*Primary Examiner* — Yanzhi Zhang
(74) *Attorney, Agent, or Firm* — KPPB LLP

(57) ABSTRACT

A method and apparatus that enables the production of micron-scale free-standing bubbles made of liquids containing surfactants are provided. The method and apparatus of the invention overcomes the limitations of conventional bubble forming techniques by using a controlled cavitation process in a liquid media.

8 Claims, 3 Drawing Sheets

METHOD AND APPARATUS FOR THE PRODUCTION OF MICROSCALE BUBBLES BY DEPRESSURIZATION CAVITATION

CROSS-REFERENCE TO RELATED APPLICATIONS

The current application is a continuation of U.S. application Ser. No. 13/089,910, filed Apr. 19, 2011, which application claims priority to U.S. Provisional Application No. 61/325,881, filed Apr. 20, 2010, the disclosures of which are incorporated herein by reference in their entireties.

FIELD OF THE INVENTION

The current invention is directed to a method and apparatus for the production of micron-scale free-standing bubbles; and more particularly to bubbles made of liquids containing surfactants.

BACKGROUND OF THE INVENTION

A free-standing bubble is a very thin film of surfactant containing fluid (such as soapy water) that forms a sphere. Such surfactant containing bubbles usually last for only a few seconds before bursting, either on their own or on contact with another object. Such surfactant bubbles can help solve complex mathematical problems of space, as they will always find the smallest surface area between points or edges. Additionally, such bubbles, when made at the micron size scale may be used for drug delivery or as tracer particles.

A surfactant containing bubble can exist because the surface layer of a liquid (usually water) has a certain surface tension, which causes the layer to behave somewhat like an elastic sheet. A surfactant containing film is extremely flexible and can produce waves based on the force exerted. However, a bubble made with a pure liquid alone is not stable and a dissolved surfactant such as soap is needed to stabilize a bubble. A common misconception is that the surfactant increases the water's surface tension, the surfactant actually does the opposite, decreasing it to approximately one third the surface tension of pure water. As such, the surfactant does not strengthen bubbles, it stabilizes them, via an action known as the Marangoni effect. As the surfactant film stretches, the surface concentration of surfactant decreases, which in turn causes the surface tension to increase. Thus the surfactant works by selectively strengthening the weakest parts of the bubble, preventing any one part of the bubble from stretching excessively. In addition, the surfactant reduces evaporation, making the bubbles last longer; but this effect is relatively small.

The spherical shape of a bubble is also due to surface tension. The sphere has the smallest possible surface area for a given volume, thus taking up a spherical shape minimizes the free surface of a bubble. This shape can be visibly distorted by air currents. However, if a bubble is left to sink in still air, it remains rather spherical, more so, for example, than the typical cartoon depiction of a raindrop. When a sinking body has reached its terminal velocity, the drag force acting on it is equal to its weight. Since a bubble's weight is much smaller in relation to its size than a raindrop's, its shape is distorted much less. (The surface tension opposing the distortion is similar in the two cases: the surfactant reduces the water's surface tension to approximately one third, but it is effectively doubled since the film has an inner and an outer surface.)

Bubbles may take on other shapes when forced to have more sides, as within another shape. Typical bubble shapes demonstrated in bubble performances are the cube shaped bubble and the tetrahedron (triangular shape with 4 sides) bubble. When all of the outsides of each shape are filled with bubble solution, a bubble may be formed inside to mimic the shape.

In conventional methods of generating bubbles, air is pushed (or blown) through liquid films that usually blocking this air stream. An illustrative example of this process is making soap bubbles by blowing air through a film of soap that is formed on a wire frame. In such a technique, the size of the wire frame (or orifice diameter in cases that a nozzle is used) determines the limiting dimension of the produced bubbles. At extremely small sizes, such as on the order of microns, it is difficult to manufacture a frame with small enough orifices to reliably generate the desired size and shape of bubbles. Accordingly, a need exists for a technique that would allow for the production of very small surfactant containing bubbles without the use of a frame.

SUMMARY OF THE INVENTION

The current invention is directed to a method and apparatus for the production of micron-scale free-standing bubbles made of liquids containing surfactants.

In one embodiment, the invention is directed to an apparatus or method of generating free-standing micron-scale bubbles including:
- providing a solution containing at least one surfactant such that the solution has a surface tension lower than that of pure water;
- placing and then pressurizing the solution in a reservoir such that a concentration of gas is dissolved therein; and
- atomizing and depressurizing the pressurized solution by releasing the solution into a region of lower pressure, such as by outputting it through a small nozzle, to generate a plurality of micron-scale bubbles, wherein the pressure differential between the pressurized and depressurized solution is sufficient to ensure cavitation of the solution occurs.

In another embodiment, the solution contains a surfactant selected from the group consisting of soap, detergent and SDL.

In still another embodiment, the solution is pressurized to a pressure of at least 2000 psi.

In yet another embodiment, the lower pressure region is at an atmospheric pressure.

In still yet another embodiment, the bubbles are on the order of about 10 microns in size.

In still yet another embodiment, the pressurizing is accomplished via one of either an air compressor or a reciprocating piston.

In still yet another embodiment, the atomizing is accomplished via a nozzle through which the solution is directed. In one such embodiment, the nozzle has an orifice of 1 mm or less.

In still yet another embodiment, the bubbles have a lifetime of at least 10 minutes.

In still yet another embodiment, the solution is gasified prior to depressurization.

BRIEF DESCRIPTION OF THE DRAWINGS

These and other features and advantages of the present invention will be better understood by reference to the following detailed description when considered in conjunction with the accompanying data and figures, wherein.

DETAILED DESCRIPTION OF THE INVENTION

The current invention is directed to a method and apparatus that enables the production of micron-scale free-standing bubbles made of liquids containing surfactants. The method and apparatus of the invention overcomes the limitations of conventional bubble forming techniques by using a controlled cavitation process in a liquid media. Although many aspects of the discussion will focus on soap bubbles, it will be understood that the surfactants used with the method and in the apparatus of the invention may include surfactants beyond soaps, and may include, for example, detergents and medical grade materials containing surfactants such as SDL.

Figure 1:
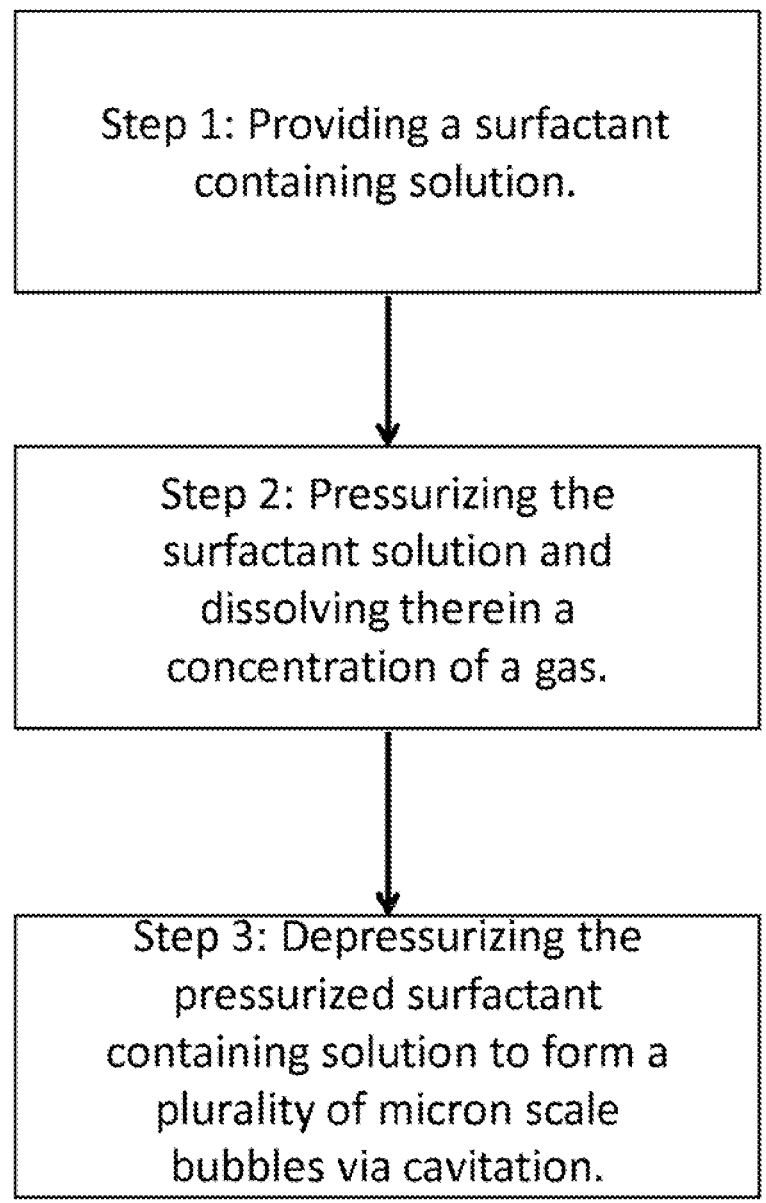
FIG. 1 provides a flow-chart of a method for producing micron-scale bubbles in accordance with an embodiment of the instant invention.

As shown in the flow-chart provided in FIG. 1, the inventive method has several steps:
- In a first step, a bubble generating liquid is prepared. As described earlier, the liquid may contain a desired amount of any suitable surfactant such as, for example, a soap, detergent or other liquid with a surface tension less than that of pure water.
- In a second step, this surfactant containing liquid is put under pressure to form a pressurized surfactant mixture.
- In a third and final step, the pressurized surfactant mixture is rapidly depressurized such that the pressure of the liquid falls below its vapor or dissolved gas partial pressure, resulting in cavitation of the pressurized liquid and the formation of bubbles.

In short, the basic concept of the invention relies on the rapid depressurization of an already pressurized mixture of liquid containing a desired amount of surfactants (or any liquid with surface tension less than that of pure water). This rapid depressurization will cause either air or other gases to leave the liquid media through gas or vapor cavitation. For the purposes of this invention, cavitation is defined as the formation of liquid or dissolved gas vapor bubbles of a flowing liquid in a region where the pressure of the liquid falls below its vapor or dissolved gas partial pressure. Cavitation occurs when a liquid is subjected to rapid changes of pressure causing the formation of gas or vapor bubbles in the lower pressure regions of the liquid. Whether a particular liquid will or will not cavitate, and therefore the conditions (i.e., initial and final pressure) under which any particular liquid must be placed to ensure bubble formation by cavitation, may be modeled in accordance with the equation:

$$Ca = \frac{p - p_v}{\frac{1}{2}\rho V^2} \qquad \text{EQ. 1}$$

where, $\rho$ is the density of the fluid, p is the local pressure, $p_v$ is the vapor pressure of the fluid, and V is a characteristic velocity of the flow. The result of this equation, the Cavitation number (Ca) is a dimensionless number used in flow calculations. It expresses the relationship between the difference of a local absolute pressure from the vapor pressure and the kinetic energy per volume, and is used to characterize the potential of the flow to cavitate.

Accordingly, it will be understood that it is possible, using this equation, for one skilled in the art to determine the initial and final conditions under which any surfactant solution will cavitate to produce bubbles in accordance with the method and apparatus of the instant invention.

Exemplary Embodiment

In this section, an example of a micron-scale bubble-generating device in accordance with the current invention is provided. The person skilled in the art will recognize that additional embodiments according to the invention are contemplated as being within the scope of the foregoing generic disclosure, and no disclaimer is in any way intended by the foregoing, non-limiting examples.

Example 1: Air Compressor Device

Figure 2:
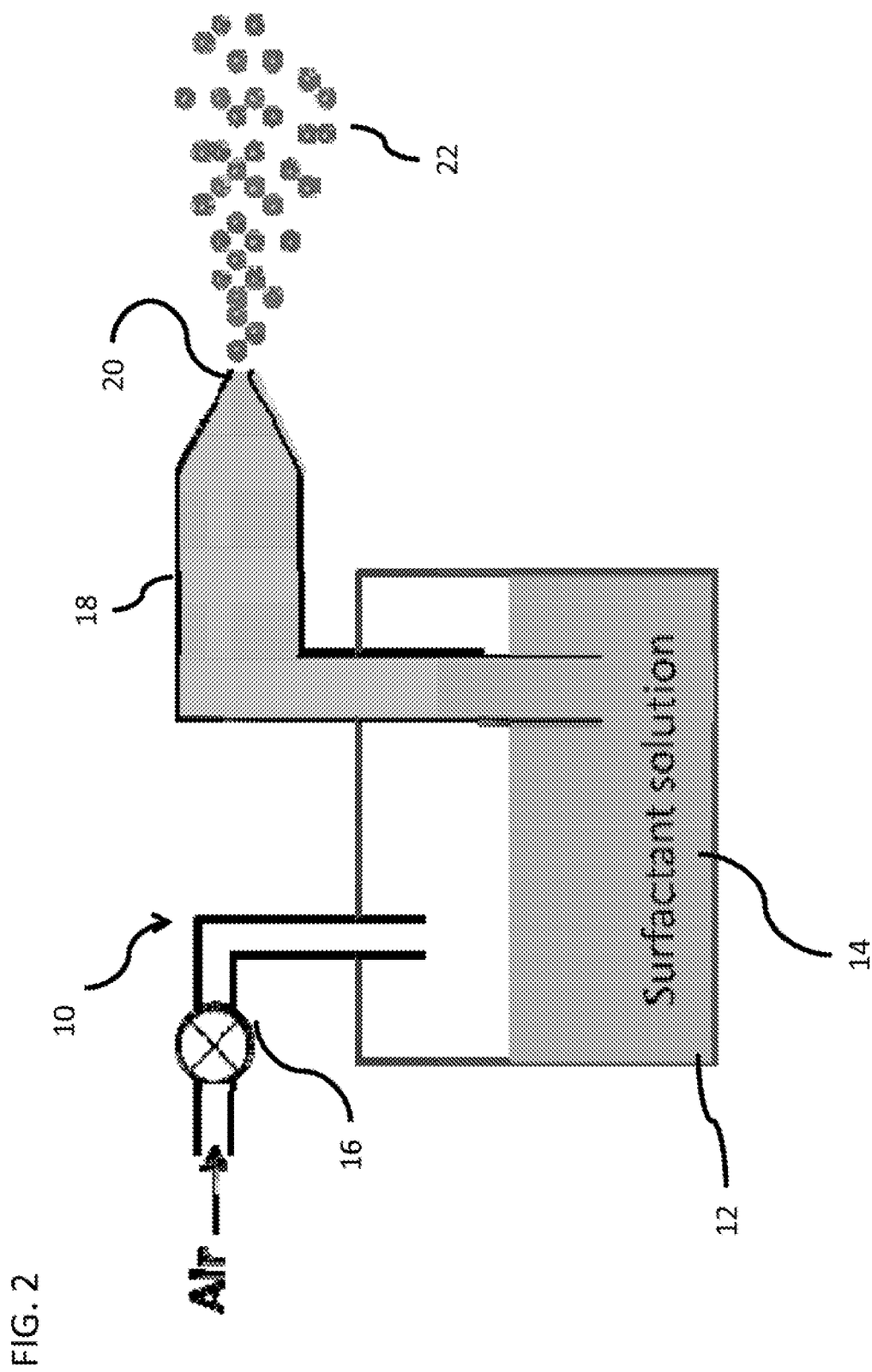
FIG. 2 provides a schematic diagram of an apparatus for producing micron scale bubbles in accordance with an embodiment of the instant invention.

FIG. 2 shows a schematic of a spray nozzle bubble generation system in accordance with the current invention. As discussed above, while this example provides an embodiment of the invention, it should be understood that other apparatuses that incorporate the pressurizing and depressurizing system described above would be incorporated into this invention, and that this specific embodiment is provided only to demonstrate the feasibility of the inventive system in producing neutrally buoyant bubbles in the 10 micron size range.

As shown in the diagram of FIG. 2, in this embodiment the bubble generation device (10) of the instant invention comprises a reservoir (12) for containing a surfactant solution (14) that can be pressurized to a desired level. By pressurizing the solution air is forced into the solution in accordance with Henry's Law:

$$p = k_H c \qquad \text{EQ. 2}$$

where p is the partial pressure of the solute in the gas above the solution, c is the concentration of the solute and $k_H$ is a constant with the dimensions of pressure divided by concentration. The constant, known as the Henry's law constant, depends on the solute, the solvent and the temperature. Accordingly, it will be understood that a significant amount of air can be dissolved into the surfactant solution during the pressurization process.

Although any pressure suitable for dissolving the desired amount of air into the surfactant containing fluid may be used, in this exemplary device, the solution at the chamber before the nozzle exit is preferably pressurized to 2000 psi. It will be understood that depending on the scale of the device and the level of gas saturation, this number may vary.

In this embodiment, an air compressor (16) is used for pressing the solution into the nozzle and supplying air for dissolution. However, it will be understood that there are any number of ways to pressurize the solution, including, for example, the use of a reciprocating piston.

The surfactant solution that is pressurized mechanically enters a nozzle (18) with an orifice (20) smaller than a millimeter, although it should be understood that the orifice may be of any suitable size to produce an atomizing mist of the surfactant solution, and, may be interchangeably interconnected with the nozzle exit. The solution is atomized as it passes through the small nozzle exit. When the atomized solution encounters the ambient pressure in air, the depressurization process follows. The dissolved air and solution rapidly expand and then collapse due to the cavitation process. The implosion process of the bubbles further fragments the initial bubble into many smaller micron size bubbles (22). Most of the bubbles created in this way are expected to have a long lifetime, that is, do not burst for a long time. Bubbles generated by the inventive bubble-generating device and method are also expected to be in the range of 10 micron size and neutrally buoyant.

Example 2: Pneumatic Piston Device

Figure 3:
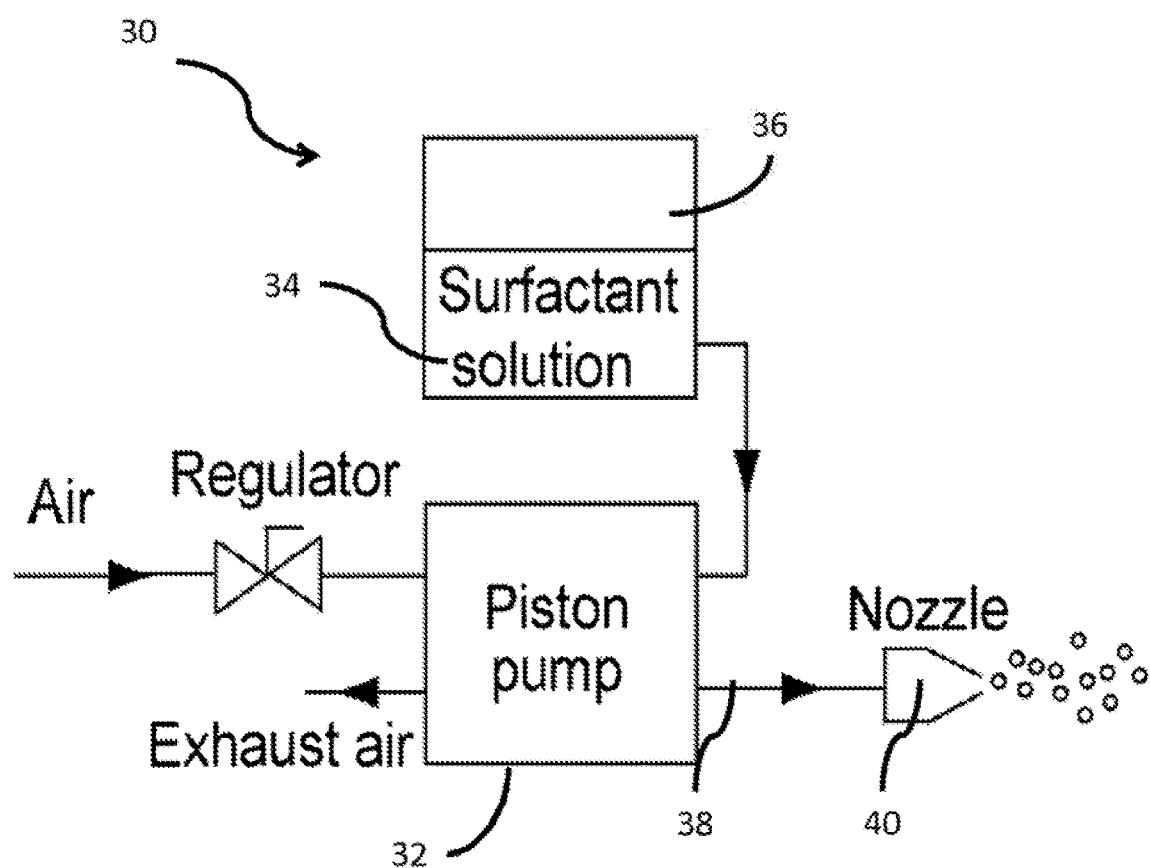
FIG. 3 provides a schematic diagram of an apparatus for producing micron scale bubbles in accordance with another embodiment of the instant invention.

Although one embodiment of the invention is provided above, it should be understood that other methods of pressurizing and depressurizing the surfactant solution may be developed. For example, FIG. 3 provides a schematic of another embodiment of the bubble-generator (30). In this embodiment, a pneumatic driven piston pump (32) (M-series, Haskel Inc.) pressurizes soap solution (34). The soap solution in a reservoir tank (36) enters the liquid inlet (38) of the piston pump, and it is pressurized by the piston pump. When the pressurized solution passes through a misting nozzle (40) having a specific orifice size, it is atomized by an atomizer inside the nozzle and depressurized by a constricting area of the nozzle.

As before, the mechanism of bubble generation for this device is a cavitation process in liquid media. The basic concept is the rapid depressurization of an already pressurized liquid containing a desired amount of surfactant below its vapor or gas partial pressure through the nozzle. When the solution encounters the ambient pressure in air, the depressurization process continues. This depressurization will cause either air or other gases to leave the liquid media through vapor or gas cavitation, which results in bubble formation.

In an experiment conducted using the device shown schematically in FIG. 3, the regulated pressure of compressed air entering the air inlet of the piston pump was 60 psi, and the area ratio of the air and liquid parts of the piston was 36:1. It can then be estimated that the pressure of the solution pressurized by the piston pump is about 2200 psi. The pressurized solution was then forced through an inlet having an orifice size of 0.25 mm (McMaster-Carr). Bubbles generated by the inventive bubble-generating device and method were formed in the range of 10 micron size and were neutrally buoyant since they were air-borne for more than 10 minutes after their generation. However, the surfactant has a critical role in precipitating the formation of bubbles and maintaining them in air. In the test a mixture of dish-wash detergent (Dawn Ultra™ dishwashing detergent) and water with a mixing ratio of 1:2 was used. When water without detergent was sprayed by the same device, most of the droplets fell down soon after injection.

In an alternative embodiment, the surfactant solution may be gasified prior to depressurization, by any known technique. Gasification of the detergent solution before bubble generating operation has shown to improve the formation of micron size bubbles.

DOCTRINE OF EQUIVALENTS

This description of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications. This description will enable others skilled in the art to best utilize and practice the invention in various embodiments and with various modifications as are suited to a particular use. The scope of the invention is defined by the following claims.

What is claimed is:

1. A method of producing free-standing micro-scale bubbles by using a controlled cavitation process comprising:
    providing an aqueous solution have a solution density (p) and containing a concentration of at least one surfactant such that the aqueous solution has a surface tension lower than that of pure water;
    disposing the solution within a pressurizing vessel defining an inner volume and having at least one gas conduit and at least one fluid outlet in fluid communication with the inner volume, wherein the at least one fluid outlet has an atomizing misting nozzle disposed at an outlet thereof disposed external to the pressurizing vessel;
    introducing a gas into the pressurizing vessel through the at least one gas inlet;
    pressurizing the pressurizing vessel to an internal pressure (p) such that a concentration of the gas is dissolved within the solution to form a pressurized solution having a solution vapor pressure ($p_v$) of the gas disposed therein; wherein the internal pressure is at least 2000 pound-force per square inch, psi;
    opening the outlet to a low pressure gaseous region having a local pressure, wherein the force imparted on the pressurized solution by the pressure differential between the internal pressure and local pressure causes the pressurized solution to flow from the inner volume of the pressurized vessel through the atomizing misting nozzle of the at least one fluid outlet to the low pressure region at a flow velocity (V) sufficient to form an atomized mist of droplets of the solution in the low pressure gaseous region;
    wherein the at least one surfactant is selected from the group consisting of soap, detergent and sodium lauryl sulfate;
    wherein the pressurized gas has a concentration (c) and the concentration and the solution vapor pressure satisfy Henry's law:

$p_v = k_H c$ and $k_H$ is Henry's law constant;
    wherein the solution density, the pressure differential between the solution vapor pressure of the atomized mist and the local pressure of the low pressure region, and the velocity of the atomized mist at the atomizing mist nozzle of the outlet are configured to produce a cavitation number (Ca) in the droplets of less than 1 as given by the equation:

$$C = \frac{p - p_v}{1/2 \rho V^2}$$

such that the cavitation occurs within the droplets of the atomized mist to produce a plurality of free-standing solution bubbles in the gaseous atmosphere of the low pressure region; and
    wherein the bubbles have a lifetime of at least 10 minutes.

2. The method of claim 1, wherein the local pressure is 1 atm.

3. The method of claim 1, wherein the internal pressure is at least 2200 psi, the local pressure is 1 atm, the atomizing misting nozzle has an orifice opening size of 1 mm or less, and the bubbles are on the order of about 10 microns in size.

4. The method of claim 1, wherein the step of pressurizing is accomplished via one of either an air compressor or a reciprocating piston.

5. The method of claim 1, wherein the atomizing misting nozzle has an orifice opening size of 1 mm or less.

6. The method of claim 1, wherein the atomizing misting nozzle has an orifice opening size of 0.25 mm or less.

7. The method of claim 1, wherein the solution has a ratio of surfactant to water of at least 1:2.

8. A method of producing free-standing bubbles comprising:
    providing an aqueous solution have a solution density ($\rho$) and containing a concentration of at least one surfactant in a ratio of surfactant to water of at least 1:2, such that the aqueous solution has a surface tension lower than that of pure water;
    disposing the solution within a pressurizing vessel defining an inner volume and having at least one gas conduit and at least one fluid outlet in fluid communication with the inner volume, wherein the at least one fluid outlet has an atomizing misting nozzle having an orifice opening of no greater than 1 mm, disposed at an outlet thereof disposed external to the pressurizing vessel;
    introducing a gas into the pressurizing vessel through the at least one gas inlet;
    pressurizing the pressurizing vessel to an internal pressure (p) of at least 2200 psi such that a concentration of the gas is dissolved within the solution to form a pressurized solution having a solution vapor pressure ($p_v$) of the gas disposed therein;
    opening the outlet to a low pressure gaseous region having a local pressure of around 1 atm, wherein the force imparted on the pressurized solution by the pressure differential between the internal pressure and local pressure causes the pressurized solution to flow from the inner volume of the pressurized vessel through the atomizing misting nozzle of the at least one fluid outlet to the low pressure region at a flow velocity (V) sufficient to form an atomized mist of droplets of the solution in the low pressure gaseous region;
    wherein the at least one surfactant is selected from the group consisting of soap, detergent and sodium lauryl sulfate;
    wherein the pressurized gas has a concentration (c) and the concentration and the solution vapor pressure satisfy Henry's law:

$$p_v = k_H c$$

and $k_H$ is Henry's law constant;
    wherein the solution density, the pressure differential between the solution vapor pressure of the atomized mist and the local pressure of the low pressure region, and the velocity of the atomized mist at the atomizing mist nozzle of the outlet are configured to produce a cavitation number (Ca) in the droplets of less than 1 as given by the equation:

$$C = \frac{p - p_v}{1/2 \rho V^2}$$

such that the cavitation occurs within the droplets of the atomized mist to produce a plurality of free-standing solution bubbles in the gaseous atmosphere of the low pressure region; and
    wherein the bubbles thus formed are on the order of about 10 microns in size and have a lifetime of at least 10 minutes.

* * * * *